United States Patent
Zhulati et al.

(10) Patent No.: US 8,244,372 B1
(45) Date of Patent: Aug. 14, 2012

(54) ELECTRICAL STIMULATION LEAD WITH STIFFENERS HAVING VARYING STIFFNESS ZONES

(75) Inventors: Enri Zhulati, Fort Worth, TX (US); Terry D. Daglow, Allen, TX (US); Brian Franz, Flower Mound, TX (US); Sojan Abraham, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 533 days.

(21) Appl. No.: 12/416,813

(22) Filed: Apr. 1, 2009

Related U.S. Application Data

(60) Provisional application No. 61/041,386, filed on Apr. 1, 2008.

(51) Int. Cl.
 *A61N 1/00* (2006.01)
 *A61B 5/01* (2006.01)
(52) U.S. Cl. ......... 607/116; 607/117; 607/122; 600/378
(58) Field of Classification Search .......... 607/116–117, 607/122; 600/378
See application file for complete search history.

(56) References Cited

U.S. PATENT DOCUMENTS

| | | | |
|---|---|---|---|
| 5,454,795 A | 10/1995 | Samson | |
| 5,605,543 A | 2/1997 | Swanson | |
| 5,843,050 A | 12/1998 | Jones et al. | |
| 6,048,338 A | 4/2000 | Larson et al. | |
| 2006/0084939 A1 | 4/2006 | Lentz | |
| 2006/0089697 A1* | 4/2006 | Cross et al. | 607/122 |
| 2006/0135961 A1* | 6/2006 | Rosenman et al. | 606/108 |
| 2007/0016165 A1 | 1/2007 | Von Oepen et al. | |
| 2008/0183263 A1 | 7/2008 | Alexander | |

* cited by examiner

*Primary Examiner* — Nicole F Lavert
(74) *Attorney, Agent, or Firm* — Craig Hoersten; Christopher S. L. Crawford; Peter R. Lando

(57) ABSTRACT

In one embodiment, a neurostimulation lead comprises an elongated body of insulative material, comprising a first end portion and a second end portion; a plurality of terminals longitudinally positioned along the first end portion; a plurality of electrodes longitudinally positioned along the second end portion; a plurality of conductors electrically coupling the plurality of electrodes to the plurality of terminals; a flexible metal longitudinal stiffener positioned within the elongated body wherein the stiffener has a plurality of longitudinal zones and each zone has a different column strength, the column strength of one or more zones of the plurality of longitudinal zones being defined by cuts or gaps in the stiffener, the stiffener causing the neurostimulation lead to exhibit a greatest amount of column strength adjacent to one end portion of the elongated body and to transition to a lower column strength toward a medial portion of the elongated body.

18 Claims, 7 Drawing Sheets

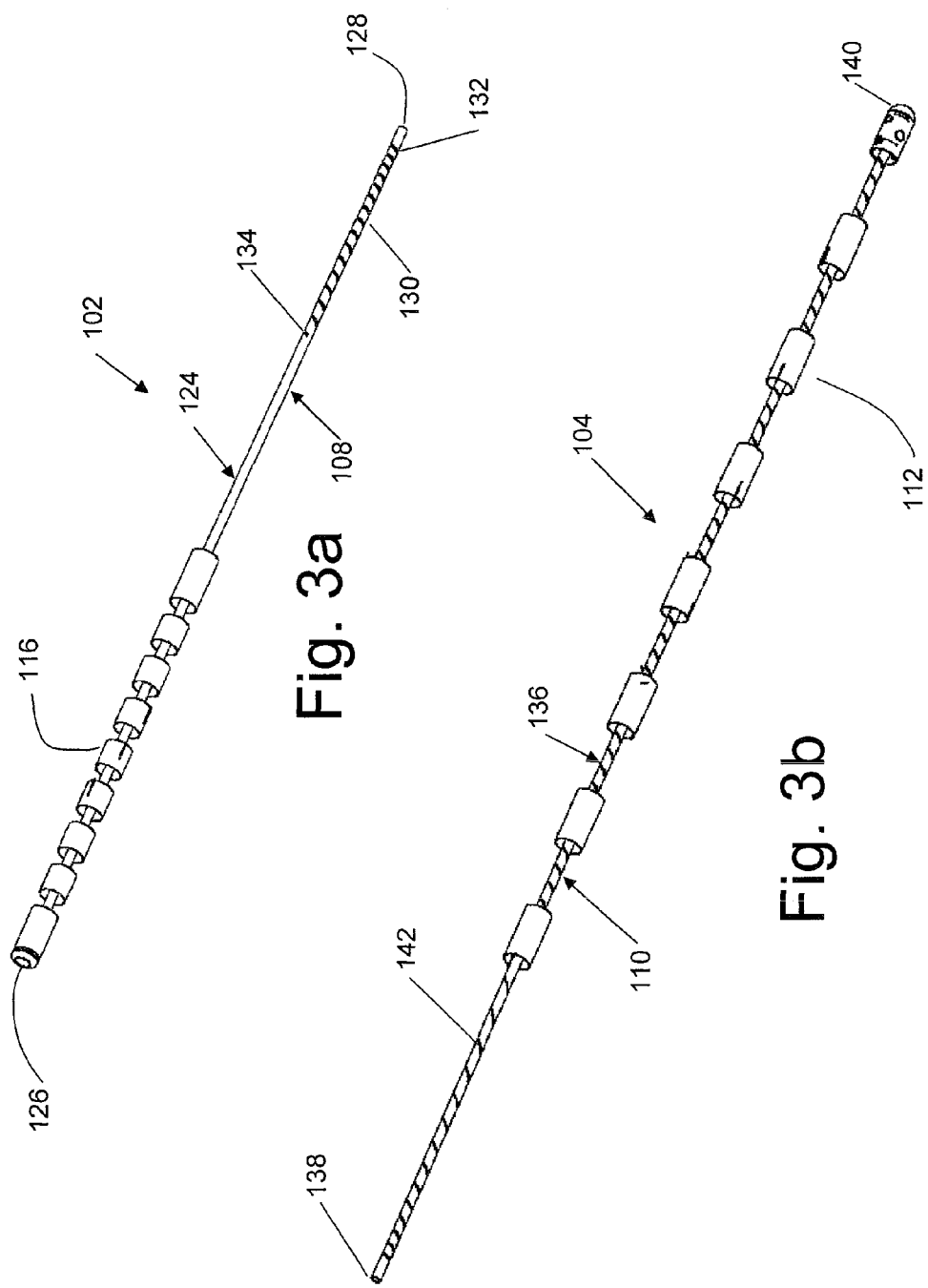

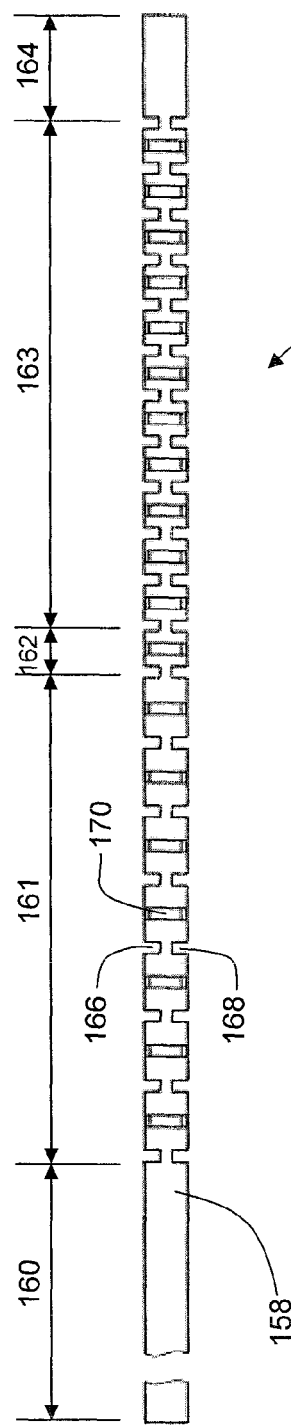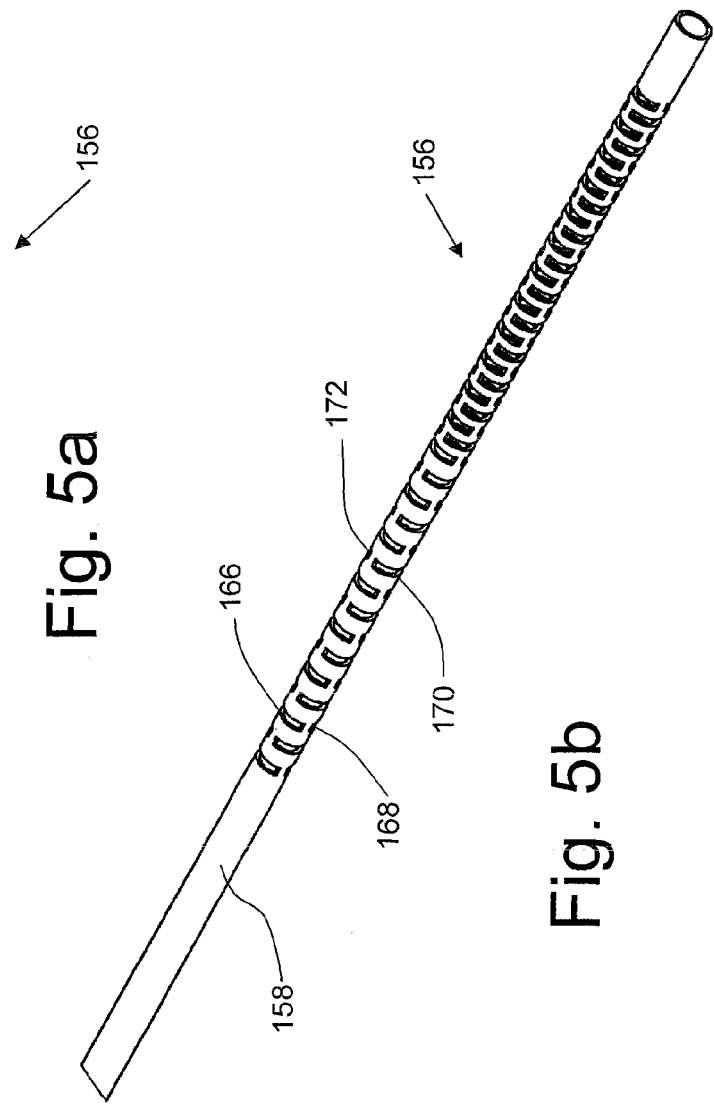
Fig. 5a
Fig. 5b

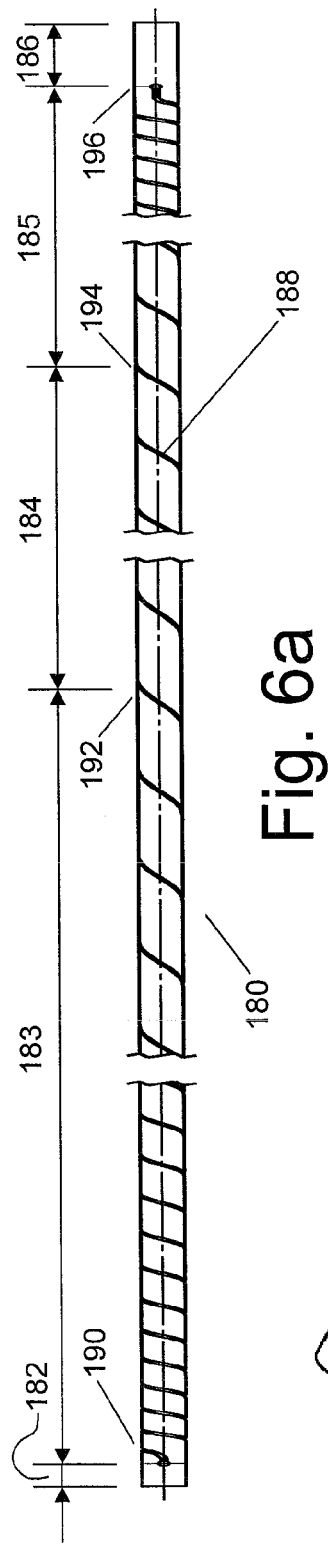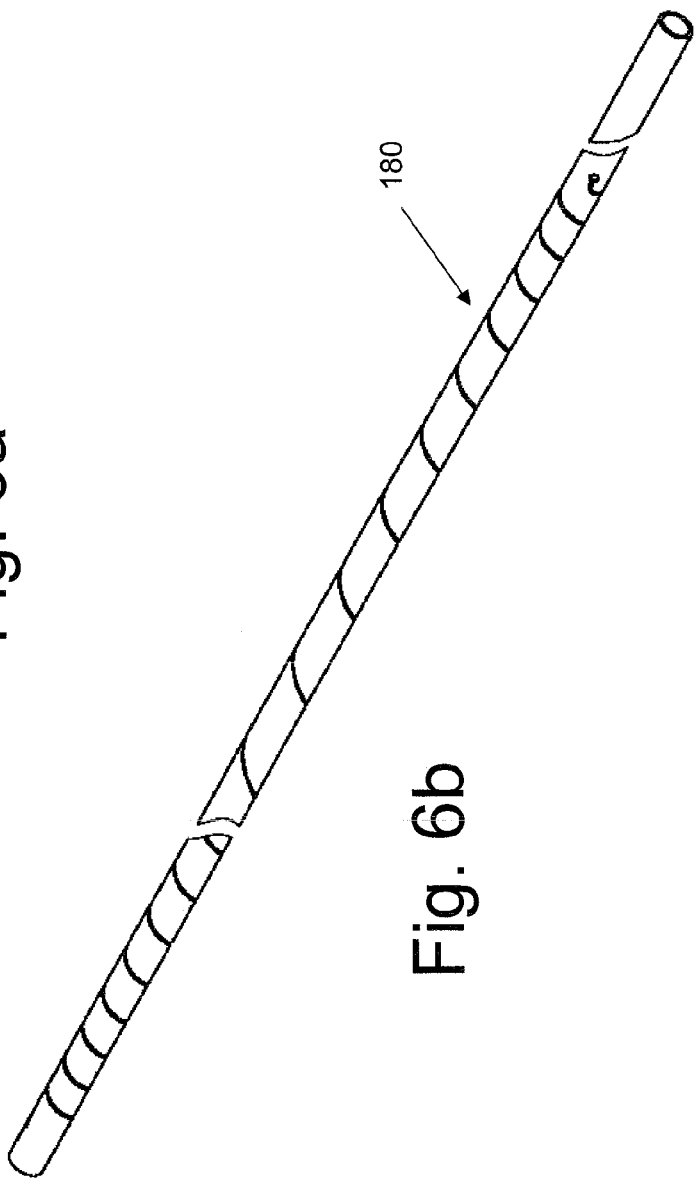
Fig. 6a
Fig. 6b

ELECTRICAL STIMULATION LEAD WITH STIFFENERS HAVING VARYING STIFFNESS ZONES

CROSS-REFERENCE TO RELATED APPLICATIONS

This application claims the benefit of U.S. Provisional Application No. 61/041,386 filed Apr. 1, 2008, which is incorporated herein by reference.

TECHNICAL FIELD

The application is generally related to electrical stimulation leads for stimulation tissue of a patient and methods of their manufacture.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine typically for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

The terminals of a stimulation lead are electrically coupled to the connectors within the header by manually pushing the proximal end of the stimulation lead into the header of the pulse generator. If the stimulation lead is improperly inserted into the header, the terminals of the stimulation lead will not be properly aligned with the connectors of the header and electrical pulses will not be properly conducted through the lead to electrodes for stimulation of tissue of the patient.

SUMMARY

In one embodiment, a neurostimulation lead comprises an elongated body of insulative material, comprising a first end portion and a second end portion; a plurality of terminals longitudinally positioned along the first end portion; a plurality of electrodes longitudinally positioned along the second end portion; a plurality of conductors electrically coupling the plurality of electrodes to the plurality of terminals; a flexible metal longitudinal stiffener positioned within the elongated body wherein the stiffener has a plurality of longitudinal zones and each zone has a different column strength, the column strength of one or more zones of the plurality of longitudinal zones being defined by cuts or gaps in the stiffener, the stiffener causing the neurostimulation lead to exhibit a greatest amount of column strength adjacent to one end portion of the elongated body and to transition to a lower column strength toward a medial portion of the elongated body.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 3a is a detailed isometric view of an exemplary proximal stiffener incorporating certain disclosed embodiments.

FIG. 3b is a detailed isometric view of an exemplary distal stiffener incorporating certain disclosed embodiments.

FIG. 4b is an isometric view of the exemplary stiffener of FIG. 4a.

FIG. 5a is a side view of an exemplary stiffener incorporating certain disclosed embodiments.

FIG. 5b is an isometric view of the exemplary stiffener of FIG. 5a.

FIG. 6a is a side view of an exemplary stiffener incorporating certain disclosed embodiments.

FIG. 6b is an isometric view of the exemplary stiffener of FIG. 6a.

DETAILED DESCRIPTION

Figure 1:
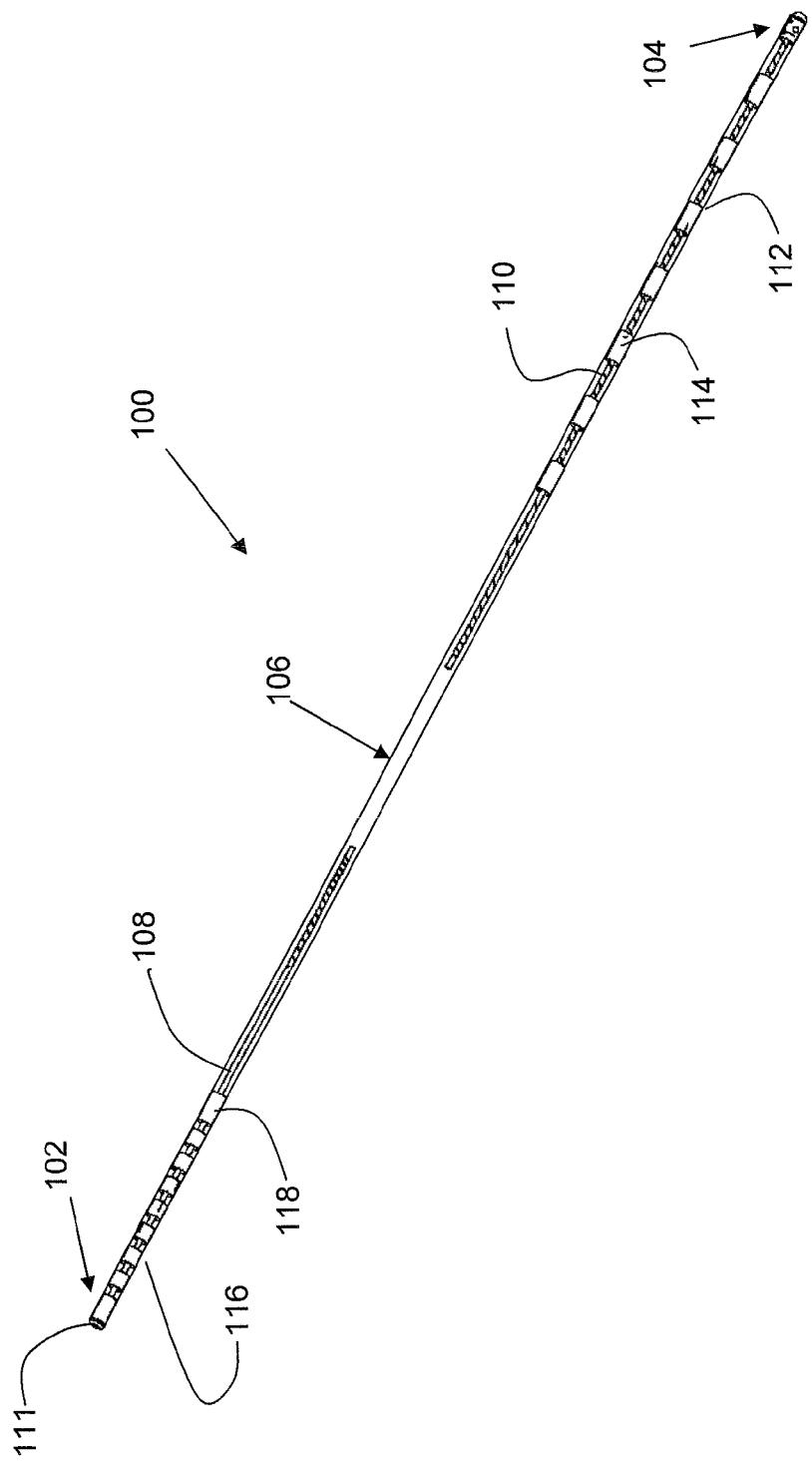
FIG. 1 is an isometric view of a lead according to a representative embodiment.

For the purposes of promoting an understanding of the principles of the present application, reference will now be made to the embodiments, or examples, illustrated in the drawings and specific language will be used to describe the same. It will nevertheless be understood that no limitation of the scope of the claims is thereby intended. Any alterations and further modifications in the described embodiments, and any further applications of the principles of the embodiments as described herein are contemplated as would normally occur to one skilled in the art to which the application relates.

Turning now to FIG. 1, there is presented one representative embodiment of a lead 100. As will be explained below, the lead 100 is generally configured to transmit one or more electrical pulses from a pulse generator to a spinal nerve, a peripheral nerve, or other tissue. The lead 100 comprises a proximal end 102 and a distal end 104. The lead 100 further comprises a flexible lead body 106 that extends from proximal end 102 to the distal end 104. As will be explained in detail later, in certain embodiments, the lead body 106 may be formed of relatively soft and compliant insulating materials such as silicone, polyurethane, polyethylene, polyamide, polyvinylchloride, PTFE, EFTE, or other suitable materials known to those skilled in the art. In certain embodiments, one or more lumens (not shown) may extend through the lead body 106 and, as will be explained later, may be used for housing one or more stiffeners or stiffening stylettes. In the illustrative embodiment, there is a proximal end stiffener 108 and a distal end stiffener 110 positioned within lumen(s) (not shown) of the lead body 106.

Adjacent to distal end 104 of lead 100 is a stimulation electrode region 112 comprising, in this embodiment, eight stimulation electrodes 114. Adjacent to proximal end 102 of lead 100 is a connector region 116 that, in this embodiment, comprises eight terminals 118. For purposes of illustration only, the lead 100 of FIG. 1 is shown with eight stimulation and eight terminals. As will be appreciated by those skilled in the art, any number of conductors, terminals, and electrodes may be utilized as desired to form lead 100. Generally, some embodiments have the same number of stimulation electrodes as terminals. In this illustrative embodiment, the stimulation electrodes and terminals are shown as metallic bands or rings.

One or more conductors (not shown) extending along a substantial portion of the lead body 106 electrically connect the terminals 118 to the stimulation electrodes 114. Although lead 100 is described as being adapted for neurostimulation according to some embodiments, lead 100 can be utilized for any suitable type of stimulation therapy, sensing application, or other medical application, such as functional electrical stimulation, cardiac stimulation, tissue ablation, gastric pacing, etc.

Figure 2:
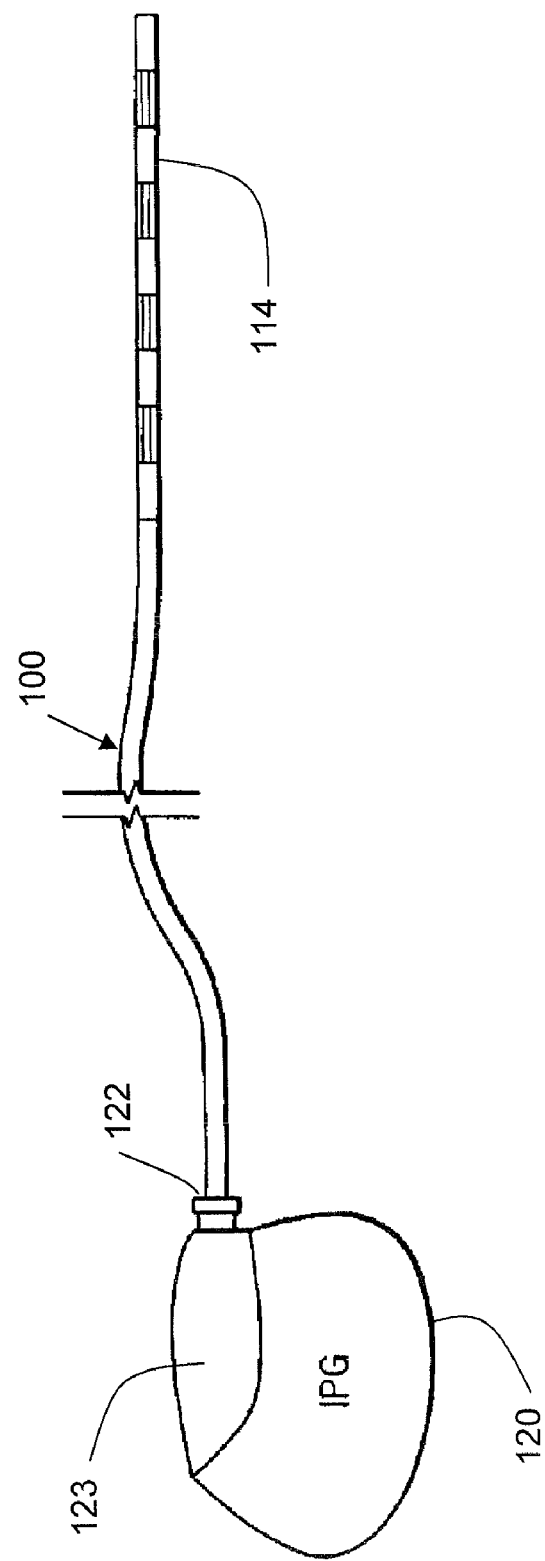
FIG. 2 is a side view illustrating the lead of FIG. 1 coupled to a pulse generator.

FIG. 2 illustrates the lead 100 connected to implantable pulse generator (IPG) 120 via a receptacle 122. As is well known in the art, an implantable pulse generator (IPG) is intended to be implanted within the body of a patient to provide electrical stimulation to treat chronic pain or another condition of the patient. An exemplary implantable pulse generator is the EON® pulse generator available from Advanced Neuromodulation Systems, Inc.

In this illustrative example, the lead 100 is connected to the implantable pulse generator 120 via the receptacle 122. The lead 100 may be detached from the pulse generator 120 as desired by applying a detaching force and removing proximal end 102 of the lead 100 from the receptacle 122. Similarly, the lead 100 may be connected to the pulse generator 120 by pushing the proximal end 102 into the receptacle 122.

As illustrated, the terminals 118 are in electrical contact with electrical connectors (not shown) within a header 123 of the pulse generator 120. A plurality of feedthrough wires (not shown) connect the electrical connectors to pulse generating circuitry (not shown) within the pulse generator 120. The pulse generator 120 sends electrical pulses to the electrical connectors, which are in electrical contact with the terminals 118. As previously discussed, the terminals 118 are themselves in electrical contact with the stimulation electrodes 114 at distal end of lead 100 because conductors (not shown) electrically connect the terminals 118 with the stimulation electrodes 114.

Thus, the pulse generator 120 may generate and send electrical pulses via the lead 100 to the stimulation electrodes 114. In use, the stimulation electrodes 114 are placed at a stimulation site (not shown) adjacent to tissue of the patient suitable for electrical stimulation. The stimulation site may be located within the epidural space as one example. The pulse generator 120 generates and delivers the electrical pulses to one or more selected electrodes according to various stimulation parameters (e.g., pulse amplitude, pulse width, pulse frequency, electrode polarity, etc.). In certain embodiments, the pulse generator 120 receives the stimulation parameters and other control signals via wireless communication with an external programming device (not shown).

Turning now to FIG. 3a, there is illustrated an isometric view of the proximal end 102 of the lead 100 with the lead body 106 and conductors removed for clarity. In this view, the stiffener 108 is shown as a tube 124 having a proximal end portion 126 and a distal end portion 128. The tube 124 could be made of Nitinol, stainless steel or other bio-compatible materials. Tube 124 preferably possesses a substantially constant diameter along its length. Although the tube 124 is used in this description, in other embodiments, the stiffener could be formed from a rod, wire or other longitudinal member having a variety of different cross sectional shapes.

At the distal end portion 128, there is a spiral cut 130 through the walls of the tube 124. As will be discussed later, the pitch of the spiral cut 130 varies as the spiral cut progresses from a distal end 132 of the spiral cut towards the proximal end 134 of the spiral cut. In this illustrative example, the pitch of the spiral cut 130 is greater towards the distal end 132 and decreases as the spiral cut progress towards its proximal end 134. This varying pitch, in turn, affects and varies the overall column strength of the tube 124 in the region of the spiral cut 130. As the pitch increases, the corresponding resistance to lateral and/or axial buckling for that portion of the tube 124 decreases. For purposes of this application, resistance to lateral and/or axial buckling within a given longitudinal length will be defined to be "column strength." For tubular structures having spiral cuts, the column strength is a function of the remaining cross section area of the tube, the diameter of the tube, and the pitch of the spiral cut.

From an end user's perspective, a higher column strength increases the "pushability" of the stiffener 108 and decreases the "flexibility" of the stiffener. The flexibility of the tube portion is inversely proportional to the column strength. In this example, therefore, the flexibility of the tube 124 increases towards the distal end 132 and decreases towards the proximal end 134 of the spiral cut 130.

In the illustrative example, the portion of the tube 124 that runs from its distal end 132 to the proximal end 134 of the spiral cut 130 is free of any cuts in its sidewalls, and thus, has a maximum cross sectional area. The tube 124, therefore, has its greatest column strength in this "solid" region, which also includes the connector region 116 of the lead 100 (See FIG. 1). So, in this example, the stiffener 108 may be thought of having at least two longitudinal zones. The first zone having a constant column strength (from the proximal end 126 of the tube 124 to the proximal end 134 of the spiral cut 130). The second zone is a longitudinal region having a reduced column strength. In the illustrative example, there are additional longitudinal zones of different column strengths which correspond to the varying change in pitch of the spiral cut 130.

This relatively large column strength of the first zone is advantageous because it allows a user to easily insert the proximal end 102 of the lead 100 into the receptacle 122 (FIG. 2) without excessive buckling. Without a stiffener, and especially for a stimulation lead having a highly compliant lead body (see U.S. Publication No. 2007/0282411), the lead 100 would tend to buckle more easily and insertion into the receptacle would be more difficult. Also, a relatively small implantable pulse generator adapted to accept a small diameter lead presents further difficulty for the proper insertion of the lead into the header of the generator. Such difficulties may potentially cause terminals of lead 100 to improperly couple or not couple at all to the electrical connectors within the header of pulse generator 120. Also, if a stiffener had a constant column strength throughout its length, the stiffener would create a stress point at its distal end of the stiffener within the relatively soft and compliant material of the lead body 106 (FIG. 1). A stress point is created in the lead 100 when there is an abrupt change in stiffness in a portion of the lead 100 where the relatively greater stiffness of a solid tube or wire meet a portion of the lead body 106 made from compliant material. The stress point could lead to material failure of the lead body 106 and/or patient discomfort.

A stiffener having at least two zones of stiffness or column strength could provide the required column strength to help insert the proximal end 102 of the lead 100 into the receptacle 122 and may have the flexibility to reduce any stress points which typically occurs within the lead body 106 if a constant column strength tube were used. A stiffener with only two zones of stiffness would provide two stress points (around the point where change in stiffness occurs and at the distal end). The magnitude of material stress within these two stress points would be significantly reduced when compared to the configuration having a single stress point. Similarly, a stiffener with multiple or varying zones of stiffness allows a gradual transition—which effectively eliminates and/or greatly reduces the magnitude of material stress within any stress points.

In sum, the proximal lead stiffener 108 provides a maximum column strength in one zone from the proximal end 126 of the tube 124 to the proximal end 134 of the spiral cut 130, which allows for easy insertion into a receptacle. In the second region from the proximal end 134 to the distal end 132, there are additional zones where the column strength is gradually reduced to eliminate or greatly reduce any stress points within the lead body 106.

FIG. 3b is a detailed isometric view of the distal end portion 140 of the lead 100 with the lead body 106 and conductors removed for clarity. In this view, the distal end stiffener 110 is shown as a tube 136 having a proximal end portion 138 and a distal end portion 140. The tube 136 could be made of Nitinol, stainless steel or other bio-compatible materials. In this illustrative embodiment, there is a spiral cut 142 through the walls of the tube 136. The pitch of the spiral cut 142 may vary along the longitudinal length of the spiral cut 142. In this illustrative example, the pitch of the spiral cut 142 may be greater towards the proximal end portion 138 and decreases as the spiral cut progress towards the distal end portion 140.

As explained above, this varying pitch affects and varies the overall column strength of the tube 136 in the region of the spiral cut 142. As the pitch increases, the corresponding column strength for that portion of the tube 136 decreases. Similarly, the flexibility of the tube portion increases because the flexibility is inversely proportional to the column strength. Thus, by varying the pitch of the spiral cut 142, the tube 136 may have different longitudinal portions or zones in which each zone has a unique column strength. Furthermore, the zones could vary from stiff to flexible to stiff, etc. depending on the application. For instance, in the region of the proximal end 138, there may be one or more zones having a relatively reduced column strength to reduce stress points in the lead body 106 (FIG. 1) as described above. In other zones within the stimulation electrode region 112, the column strength could increase or vary to make implantation easier for the surgeon or to correspond with anatomical features of the application and/or patient. For example, the distal end stiffener 110 may be five longitudinal zones, where each zone has a different column strength corresponding to surgical implantation techniques and patient anatomy.

Figure 4A:
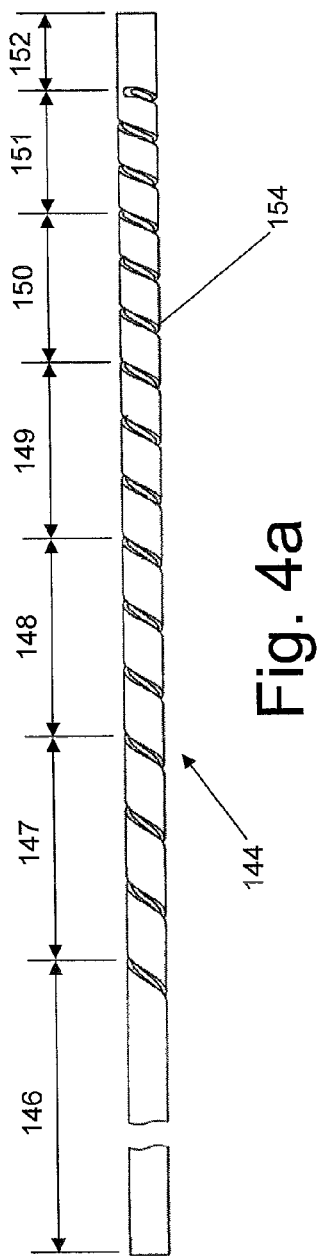
FIG. 4a is a side view of an exemplary stiffener incorporating certain disclosed embodiments.
Figure 4B:
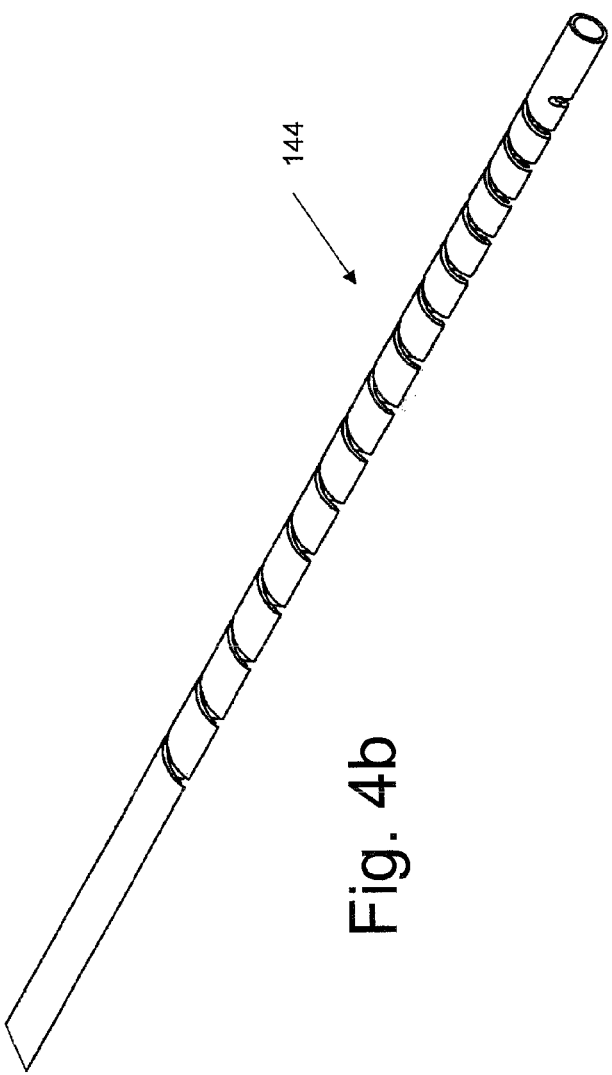

Turning now to FIG. 4a, there is a side view of an example embodiment of a stiffener 144. FIG. 4b is an isometric view of the example embodiment 144. As illustrated, the stiffener 144 has six longitudinal zones 146 to 152 of varying column strength created a spiral cut 154 (or lack thereof). In this example, the pitch of the spiral cut is maximum in the zone 151 (for example 0.02) and is minimum in the zone 147 (for example 0.04). There is no cut in zone 146 and the tip portion 152. Thus, the column strength of the stiffener is maximum in zone 146, relatively stiff in zone 147 and is minimum in zone 151. Such a configuration could be used for a proximal end stiffener of a lead as discussed previously.

Although a spiral having varying pitch cut in a tube is but one example of a stiffener having a variable column strength, other implementations are possible to provide variable column strength. For example, stiffeners having varying stiffness zones could also be created by using different patterns of cuts or slots formed in the longitudinal member. The stiffener shown in FIGS. 5a and 5b is one such example.

FIG. 5a is a side view of another embodiment of a stiffener 156. FIG. 5b is an isometric view of the stiffener 156. In this example embodiment, the column strength varies due a series of alternating lateral cuts or slots made within the walls of a tube 158. In this example embodiment, the stiffener 156 has five longitudinal zones 160 to 164 of varying column strength created by a change in spacing of the lateral cuts. As illustrated in FIG. 5b, there may be a first series of lateral slots or cuts 166 and a second series of opposing cuts 168 positioned across from the lateral cuts 166 (forming a first plurality of pairs of opposing later cuts). Longitudinally spaced within the series of lateral cuts 166 and 168, there may be another series of interspersed cuts 170 and a corresponding series of opposing lateral cuts 172 forming a second plurality of pairs of opposing lateral cuts. In certain embodiments, the lateral cuts 170 and 172 may be orientated substantially perpendicular to the lateral cuts 166 and 168. In other embodiments, the lateral cuts could be orientated at other angles or angles which vary along the length of the stiffener 156.

In this example, the spacing of the lateral cuts is maximum in the zone 163 (for example 0.02 inch) and is minimum in the zone 161 (for example 0.03 inch). In this embodiment, zone 162 is a transition zone. Furthermore, there are no cuts in zone 160 and the tip portion 164. Thus, the column strength of the stiffener 156 is maximum in zone 160, relatively stiff in zone 161 and is minimum in zone 163. Such a configuration could also be used for a proximal end stiffener of a lead as discussed previously.

Turning now to FIG. 6a, there is a side view of an example embodiment of a stiffener 180 which may be used at a distal end of a lead. FIG. 6b is an isometric view of the example embodiment 180. As illustrated, the stiffener 180 has five longitudinal zones 182 to 186 of varying column strength created a spiral cut 188 (or lack thereof). In this example, however, the pitch of the spiral cut 188 varies within certain longitudinal zones.

In certain embodiments, there is no cut in the end portions (zone 182 and the tip portion 186). In zone 183, the pitch of the spiral cut 188 varies from a lesser value at a proximal end 190 of the zone to a greater value at a distal end 192 of the zone. In zone 184, the pitch may remain constant. In zone 185, the pitch of the spiral cut 188 may vary from a greater value at the proximal end 194 to a lesser value at the distal end 196 of the zone. Consequently, the column strength of the stiffener 188 is maximum in zones 182 and 186. In zone 183, the column strength varies from a relatively low value at the proximal end 190 of the zone to a relatively high value at the distal end 192. The column strength remains constant in zone 184. In zone 185, the column strength varies from a relatively higher value at the proximal end 194 of zone 185 to a lower value at the distal end 196.

Such a configuration for a distal end stimulation stiffener may keep the lead from buckling when implanted in the dorsal column due to gravity or patient movements. In some embodiments, the stimulation end stiffener may also reduce the likelihood of lead buckling off the needle during implant and pushing. In certain embodiments, the stimulation end stiffener may make it easier to steer the lead. In certain regions, the column strength of the end of the lead may be weaker so that it compliments and complies with the bend of the stylet.

The stiffener 180 may be dimensioned to conform to the anatomy of a patient. By way of an illustrating example, in a certain embodiment of a tubular stiffener made from a superelastic Nitinol alloy having a similar configuration to that illustrated in FIGS. 6a and 6b, the overall length of the stiffener could be approximately 7.8 inches. The exterior diameter of the stiffener may be 0.021" and an interior diameter of 0.017." In such an example, the spiral cut 188 may have a width of 0.003". The zone 183 may have a length of approximately 1.96 inches. The pitch of the spiral cut 188 may vary from 0.02" inches at the proximal end 190 of the zone 183 to 0.08" at the distal end 192 of the zone. The pitch of the spiral cut 188 in zone 184 may be 0.1". In zone 185, the pitch of the spiral cut 188 may vary from 0.08" at the proximal end 194 of the zone to 0.02" at the distal end 196 of the zone. The foregoing dimensions are provided by way of example only, and are not meant to limit the scope of the present invention in any manner.

Various methods of making lead bodies with conductors are known in the art. Certain methods of making a lead body with conductors are disclosed in U.S. Publication No. 2005/027340, entitled "System and Method for Providing a Medical Lead Body having Dual Conductor Layers," filed on Jul. 29, 2003 and in U.S. Pat. No. 6,216,045, entitled "Implantable Lead and Method of Manufacture," filed on Apr. 26, 1999, the disclosures of which are hereby incorporated by reference for all purposes. In one embodiment, the stimulation lead is adapted to exhibit appreciable elongation under relatively low stretching forces. For example, the stimulation lead may be adapted to elongate at least 15%, 25%, or more when a relatively low stretching force (e.g., 1 or 2 pounds or less) is applied to the lead. Fabrication of stimulation leads adapted in this manner is described in U.S. Publication No. 2007/0282411, entitled "Compliant Electrical Stimulation Leads and Methods of Fabrication," filed on Mar. 30, 2007, the disclosure of which is incorporated herein by reference for all purposes.

Figure 7:
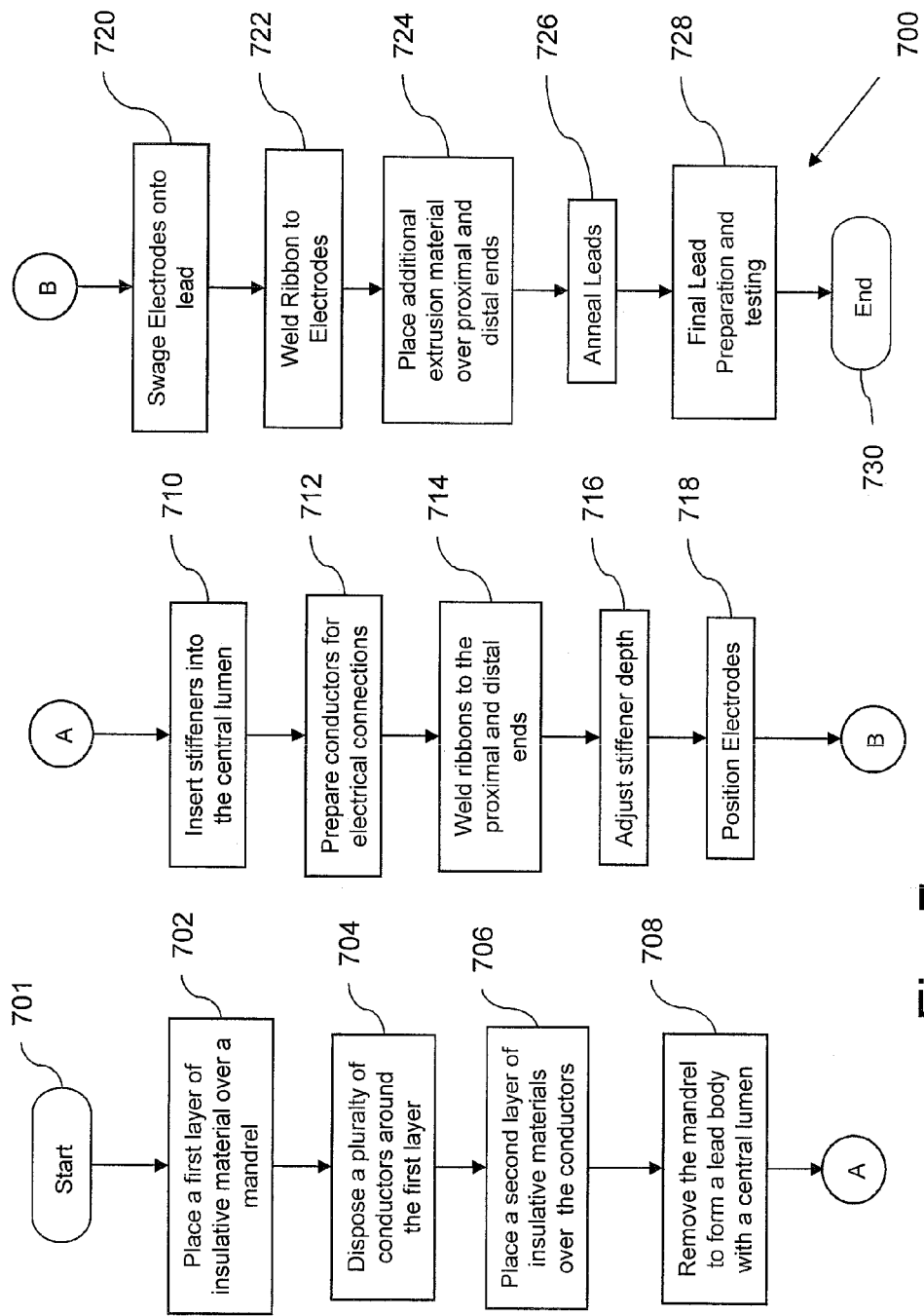
FIG. 7 is a flow chart illustrating a process of making certain disclosed embodiments.

FIG. 7 is a process flow chart illustrating one embodiment of a method 700 for making a lead incorporating various features discussed above. The process begins at step 701. In step 702, an inner layer of extrusion material may be placed on a mandrel to begin forming the lead body. A plurality of conductors may be provided where each conductor is coated with extrusion material. Each coated conductor may be wrapped around the inner layer of the extrusion material on the mandrel (step 704). An outer layer of extrusion material may then be placed over the plurality of conductors (step 706). Heat shrink tubing is then placed over the outer layer and the lead body assembly may be heated to melt the extrusion material. The melted extrusion material is compressed around the plurality of conductors as the heat shrink tubing shrinks. The lead body may then be cooled and the heat shrink tubing may be removed. The solidified extrusion material forms the lead body. The lead body may then be removed from the mandrel which leaves a longitudinal lumen in the lead body (step 708).

In step 710, stiffeners incorporating various aspects disclosed above may now be inserted into the longitudinal lumen. In certain embodiments, the stiffeners may be inserted into both the proximal ends and the distal ends. In other embodiments, a stiffener may only be inserted into either the proximal or distal end depending on the application for the lead.

In step 712, the conductors may be prepared to electrically connect with electrodes. Such preparation may include laser ablating the electrode sites on the proximal and distal ends of the lead body. Once the sites are ablated, the conductors may be pulled to the surface.

In some embodiments, distal ends of a plurality of ribbons corresponding to the number of electrodes may be laser welded to conductors at the electrode sites. (step 714). In certain embodiments, the electrodes may now be slid over the ribbons. In step 716, the stiffener depth may now be adjusted. The electrodes may then be longitudinally positioned along the lead body (step 718). In certain embodiments, a fixture indicating the proper spacing may be used. Once in place, the electrodes may be pre-crimped.

The electrodes may then be swaged onto the lead (step 720). The stiffener provides a solid center which provides the necessary compression needed to swage the respective electrode over the lead body. After the electrodes are compressed by the swaging, the proximal ends of each ribbon may be welded to an edge of a corresponding electrode (step 722). In step 724, additional extrusion material may then be placed over the proximal and distal ends of the lead. The leads may then be annealed (step 726). In step 728, final preparation of the leads, including various testing, may then be accomplished using methods known to those skilled in the art. In certain embodiments, the process ends at step 730.

In some embodiments, therefore, leads may be manufactured integral with stiffeners having varying zones of stiffness. When used as described in the above manufacturing process, such stiffeners provide the necessary compression force to allow swaging of the electrodes to the leads while reducing the likelihood of undesirable stress points developing within the lead at a later point in time.

In other embodiments, electrodes may be coupled to the leads using other methods known to those skilled in the art. In such embodiments, stiffeners having varying zones of stiffness may be used to enhance the steerability of the lead during implantation or during coupling of the lead to the pulse generator. In such embodiments, the leads do not have to be formed integral with the stiffeners. The stiffeners may be inserted into the central lumen of the lead at a later time.

In certain embodiments, the leads and stiffeners could be provided as part of a kit. In such embodiments, the leads may have a proximal stiffener to aid in the coupling of the lead to a pulse generator. The leads may also be supplied with a plurality of stiffeners, where each stiffener has different length longitudinal zones of stiffness corresponding to the likely sizes and shapes of patient anatomy. In certain embodiments, a plurality of stylets may also be used with a single stiffener. For instance, the stylets may be used in conjunction with a distal end stiffener and may have complimentary structural properties. The stylets may have longitudinal stiffness zones which are designed to compliment the longitudinal stiffness zones of the corresponding stiffeners to increase steerability during implantation. Upon removal of the stylet, the end stiffener may then have longitudinal stiffness zones which closely correspond with a patient's anatomy to reduce buckling during use. Such a kit would allow a surgeon to have greater flexibility in choosing the correct stiffener and stylet to use in an individual patient.

Once implanted, various disclosed embodiments of the distal end stimulation stiffener may keep the lead from buckling when implanted in the dorsal column due to gravity or patient movements. Specifically, in the space between the distal stimulation end and an anchor. Buckling in this area is undesirable because if the lead buckles, the stimulation end will lose its position and the effectiveness of stimulation may be diminished. In some embodiments, the stimulation end stiffener may also reduce the likelihood of lead buckling off the needle during implant and pushing. In certain embodiments, the stimulation end stiffener may make it easier to steer the lead. In certain regions, the column strength of the end of the lead may be weaker so that it compliments and complies with the bent of the stylet. Additionally, various embodiments of the stimulation end stiffener may assist the physician to steer through impediments or obstructions during the implantation procedure.

Any advantages and benefits described above may not apply to all embodiments of the invention and may not apply to all of the claims. The foregoing description of the embodiments of the invention has been presented for the purposes of illustration and description. It is not intended to be exhaustive or to limit the invention to the precise form disclosed. Many combinations, modifications and variations are possible in light of the above teaching. Undescribed embodiments which have interchanged components are still within the scope of the present invention. It is intended that the scope of the invention be limited not by this detailed description, but rather by the claims appended hereto.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed:

1. A neurostimulation lead comprising:
an elongated body of insulative material, comprising a longitudinal lumen, a first end portion, and a second end portion;
a plurality of terminals longitudinally positioned along the first end portion;
a plurality of electrodes longitudinally positioned along the second end portion;
a plurality of conductors electrically coupling the plurality of electrodes to the plurality of terminals;
a flexible metal longitudinal stiffener positioned within the lumen, the stiffener including at least a first and second region with the first region being solid walled and the second region comprising one or more spiral cuts including at least a first pitch and a second pitch, wherein the second pitch is different than the first pitch, the stiffener causing the neurostimulation lead to exhibit a greatest amount of column strength adjacent to one end portion of the elongated body and a transition to a lower column strength toward a medial portion of the elongated body.

2. The neurostimulation lead of claim 1, wherein the longitudinal stiffener is selected from a group consisting of a rod, a wire, and a tubular structure.

3. A neurostimulation lead comprising:
an elongated body of insulative material, comprising a longitudinal lumen, a first end portion, and a second end portion;
a plurality of terminals longitudinally positioned along the first end portion;
a plurality of electrodes longitudinally positioned along the second end portion;
a plurality of conductors electrically coupling the plurality of electrodes to the plurality of terminals;
a flexible metal longitudinal stiffener positioned within the lumen with the stiffener including at least a first and second region with the first region being solid walled and the second region including slots, the stiffener causing the neurostimulation lead to exhibit a greatest amount of column strength adjacent to one end portion of the elongated body and to transition to a lower column strength toward a medial portion of the elongated body, wherein the stiffener comprises:
an elongated member having a longitudinal axis and first plurality of pairs of opposing lateral slots longitudinally spaced at a first distance along a first stiffness zone;
a second plurality of pairs of opposing lateral slots longitudinally spaced at the first distance along the first stiffness zone, wherein the second plurality of pairs of opposing lateral slots are longitudinally interdispersed among the first plurality of pairs of opposing lateral slots and are angularly offset about the longitudinal axis from the first plurality of pairs of opposing lateral slots,
a third plurality of pairs of opposing lateral slots longitudinally spaced at a second distance along a second stiffness zone, and
a fourth plurality of pairs of opposing lateral slots longitudinally spaced at the second distance along the second stiffness zone, wherein the fourth plurality of pairs of opposing lateral slots are longitudinally interdispersed among the third plurality of pairs of opposing lateral slots and are angularly offset about the longitudinal axis from the third plurality of pairs of opposing lateral slots.

4. The neurostimulation lead of claim 3, wherein the longitudinal stiffener is selected from a group consisting of a rod, a wire, and a tubular structure.

5. A neurostimulation lead comprising:
an elongated body of insulative material, comprising a first end portion and a second end portion;
a plurality of terminals longitudinally positioned along the first end portion;
a plurality of electrodes longitudinally positioned along the second end portion;
a plurality of conductors electrically coupling the plurality of electrodes to the plurality of terminals;
a flexible metal longitudinal stiffener positioned within the elongated body wherein the stiffener including at least a first and second region with the first region being solid walled and the second region including at least one cut or gap, the stiffener having has a plurality of longitudinal zones and each zone has a different column strength, the column strength of one or more zones of the plurality of longitudinal zones being defined by the cut or gap in the stiffener, the stiffener causing the neurostimulation lead to exhibit a greatest amount of column strength adjacent to one end portion of the elongated body and to transition to a lower column strength toward a medial portion of the elongated body.

6. The neurostimulation lead of claim 5, wherein the longitudinal stiffener is slideably removable from a lumen of the elongated body.

7. The neurostimulation lead of claim 5, wherein the longitudinal stiffener is embedded within or attached to insulative material of the elongated body.

8. The neurostimulation lead of claim 5, wherein the longitudinal stiffener is positioned at the first end portion.

9. The neurostimulation lead of claim 8, further comprising a second longitudinal stiffener positioned at the second end portion, wherein the second stiffener has a plurality of longitudinal zones and each zone has a different column strength.

10. The neurostimulation lead of claim 5, wherein the longitudinal stiffener comprises a tubular structure having a spiral cut within a longitudinal portion wherein the pitch of the spiral varies.

11. The neurostimulation lead of claim 5, wherein the longitudinal stiffener comprises a tubular structure having a plurality of lateral slots cut therein in which the spacing of the lateral cuts varies across the longitudinal zones.

12. A kit for neurostimulation, comprising:
    an implantable pulse generator having a header housing a receptacle with a plurality of electrical connectors;
    a lead comprising:
    a longitudinal body of insulative material comprising a lumen, a proximal end portion, and a distal end portion;
    a plurality of terminals longitudinally positioned along the proximal end portion such that the terminals electrically connect with the plurality of electrical connectors when the proximal end portion of the longitudinal body is coupled to the receptacle of the implantable pulse generator;
    a plurality of electrodes longitudinally positioned along the distal end portion;
    a plurality of conductors spaced within the longitudinal body and electrically coupling the plurality of terminals to the plurality of electrodes;
    a flexible metal longitudinal stiffener including at least a first and second region with the first region being solid walled and the second region including at least one cut or gap, wherein (i) the stiffener comprises an outer diameter sized to be positioned within the lumen, (ii) the stiffener comprises a plurality of longitudinal zones with each zone comprising a different column strength, and (iii) the column strength of one or more zones of the plurality of longitudinal zones being defined by the cut or gap or in the stiffener.

13. The kit of claim 12 wherein the longitudinal stiffener comprises a spiral cut along a substantial length of the stiffener.

14. The kit of claim 13 wherein a pitch of the spiral cut is varied along a substantial length of the longitudinal stiffener.

15. The kit of claim 13 wherein the longitudinal stiffener comprises:
    a first plurality of pairs of opposing lateral slots longitudinally spaced at a first distance along a first stiffness zone;
    a second plurality of pairs of opposing lateral slots longitudinally spaced at the first distance along the first stiffness zone, wherein the second plurality of pairs of opposing lateral slots are longitudinally interdispersed among the first plurality of pairs of opposing lateral slots and are angularly offset about the longitudinal axis from the first plurality of pairs of opposing lateral slots,
    a third plurality of pairs of opposing lateral slots longitudinally spaced at a second distance along a second stiffness zone, and
    a fourth plurality of pairs of opposing lateral slots longitudinally spaced at the second distance along the second stiffness zone, wherein the fourth plurality of pairs of opposing lateral slots are longitudinally interdispersed among the third plurality of pairs of opposing lateral slots and are angularly offset about the longitudinal axis from the third plurality of pairs of opposing lateral slots.

16. The kit of claim 12 wherein the kit further comprises:
    a plurality of stylets, wherein the longitudinal stiffener comprises an inner diameter sized to permit each stylet of the plurality of stylets to be inserted through the stiffener.

17. The kit of claim 12 wherein the longitudinal stiffener, when inserted into the lumen, causes the neurostimulation lead to exhibit a greatest amount of column strength adjacent to one end portion of the elongated body and to transition to a lower column strength toward a medial portion of the elongated body.

18. The kit of claim 12 wherein the longitudinal stiffener comprises a greatest amount of column strength in first and second zones at each end of the stiffener, a lowest amount of column strength in a third and fourth zones respectively adjacent to the first and second zones, and lowest amount of column strength in a fifth zone at a medial portion of the stiffener.

\* \* \* \* \*

UNITED STATES PATENT AND TRADEMARK OFFICE
CERTIFICATE OF CORRECTION

| | | |
|---|---|---|
| PATENT NO. | : 8,244,372 B1 | Page 1 of 1 |
| APPLICATION NO. | : 12/416813 | |
| DATED | : August 14, 2012 | |
| INVENTOR(S) | : Enri Zhulati et al. | |

It is certified that error appears in the above-identified patent and that said Letters Patent is hereby corrected as shown below:

Column 10, line 64, in claim 5, "having has" to read as --has--;

Column 12, line 3, in claim 12, "or gap or in" to read as --or gap in--.

Signed and Sealed this
Ninth Day of October, 2012

David J. Kappos
*Director of the United States Patent and Trademark Office*